US012115188B2

(12) United States Patent
Perruche et al.

(10) Patent No.: US 12,115,188 B2
(45) Date of Patent: Oct. 15, 2024

(54) SUPERNATANT FROM A COCULTURE OF MACROPHAGES AND IRRADIATED LEUKOCYTES, FOR CONTROLLING TUMOUR PROGRESSION OR RESTORING ANTI-TUMOR IMMUNITY

(71) Applicant: MED' INN' PHARMA, Placey (FR)

(72) Inventors: Sylvain Perruche, Placey (FR); Francis Bonnefoy, Les Auxons (FR); Mélanie Couturier, Vy-les-Filain (FR)

(73) Assignee: MED' INN' PHARMA, Placey (FR)

( * ) Notice: Subject to any disclaimer, the term of this patent is extended or adjusted under 35 U.S.C. 154(b) by 779 days.

(21) Appl. No.: 17/252,818

(22) PCT Filed: Jun. 20, 2019

(86) PCT No.: PCT/EP2019/066406
§ 371 (c)(1),
(2) Date: Dec. 16, 2020

(87) PCT Pub. No.: WO2019/243544
PCT Pub. Date: Dec. 26, 2019

(65) Prior Publication Data
US 2021/0145874 A1    May 20, 2021

(30) Foreign Application Priority Data
Jun. 21, 2018 (FR) ...................... 1800636

(51) Int. Cl.
*A61K 35/15* (2015.01)
*C12N 5/0786* (2010.01)

(52) U.S. Cl.
CPC ............ *A61K 35/15* (2013.01); *C12N 5/0645* (2013.01); *C12N 2502/1157* (2013.01); *C12N 2502/30* (2013.01)

(58) Field of Classification Search
None
See application file for complete search history.

(56) References Cited

U.S. PATENT DOCUMENTS 10,653,758 B2 *   5/2020  Perruche ............ A61K 39/0005
11,793,865 B2 * 10/2023  Perruche ............... C07K 14/435
2008/0089875 A1    4/2008  Cui et al.

FOREIGN PATENT DOCUMENTS

| CN | 1237909 A | 12/1999 |
| CN | 1270630 A | 10/2000 |
| CN | 103796680 A | 5/2014 |
| CN | 107530376 A | 1/2018 |
| EP | 2941257 A1 | 11/2015 |
| WO | 9903976 A2 | 1/1999 |
| WO | 0128573 A2 | 4/2001 |
| WO | 2014106666 A1 | 7/2014 |
| WO | 2016132366 A1 | 8/2016 |

OTHER PUBLICATIONS

Cantor (2017) "Physiologic Medium Rewires Cellular Metabolism and Reveals Uric Acid as an Endogenous Inhibitor of UMP Synthase", Cell, 169: 258-72. (Year: 2017).*
Shibata T et al. "Apoptotic neutrophils and nitric oxide regulate cytokine production by IFN-@c-stimulated macrophages" Cytokine, Academic Press Ltd, Philadelphia, PA, US, vol. 53, No. 2, Feb. 1, 2011 (Feb. 1, 2011), pp. 191-195, [retrieved on Jan. 10, 2011] ISSN: 1043-4666, XP027590037 see abstract, pp. 192-193.
Zhang Qi et al. "Resolution of Cancer-Promoting Inflammation: A New Approach for Anticancer Therapy." Frontiers in Immunology 2017, vol. 8, 2017, p. 71 ISSN: 1664-3224, XP002789002 the whole document.

* cited by examiner

Primary Examiner — Robert M Kelly
(74) Attorney, Agent, or Firm — Volpe Koenig

(57) ABSTRACT

The invention relates to a method for the resolution of pro-tumour inflammation by means of a pharmaceutical preparation. Leukocytes are isolated from the buffy coat obtained from whole blood and a portion of the leukocytes is placed in a first pouch receiving a differentiation factor and stored in conditions that preserve cellular viability for several days, before a defined, fresh culture medium is supplied, after which said leukocyte portion is left to rest for a further several days, which results in the production of macrophages. A further portion of the leukocytes is placed in a second pouch and irradiated therein. The two pouches are then mixed and the supernatant is recovered to serve as pharmaceutical preparation. The invention also relates to the use in the treatment of cancers, either alone or in combination with other therapies, in human and veterinary medicine.

2 Claims, 4 Drawing Sheets

SUPERNATANT FROM A COCULTURE OF MACROPHAGES AND IRRADIATED LEUKOCYTES, FOR CONTROLLING TUMOUR PROGRESSION OR RESTORING ANTI-TUMOR IMMUNITY

FIELD OF THE INVENTION

The present invention relates to a method for resolving pro-tumor inflammation by means of a pharmaceutical preparation.

BACKGROUND

The inflammatory reaction is a biological process which is part of the natural defense reactions of the organism but is also associated with a multitude of pathological reactions.

In particular inflammation causes inflammatory diseases such as inflammatory diseases of the intestine, like Crohn's disease and rheumatoid arthritis, but it is also involved in the pathogenesis of obesity, diabetes and neurological disorders such as depression. Pro-inflammatory factors such as proinflammatory cytokines are involved in and support inflammation in obesity, tumorigenesis and during the progression of cancer. Indeed, chronic inflammation plays an important role in promoting the failure of treatment of the tumor by the immune system and maintaining the development of the tumor. Inflammation remains an acute risk factor for cancer.

Chronic inflammation can be related to a partial or incomplete resolution of the inflammatory reaction, which can be encouraged by genetic, environmental or infection factors. Chronic inflammation is involved in particular in the progression of cancers caused by viral infections, such as inflammation associated with the papilloma virus (HPV) which increases the risk of cancer of the neck, and inflammation associated with the hepatitis B and C virus and the appearance of hepato-carcinoma or also with *Helicobacter pylori* and the development of adenocarcinoma or lymphoma. Chronic inflammation in auto-immune diseases such as Crohn's disease or ulcerative colitis is also associated with an increased risk of developing colorectal cancer. Lastly, inflammation caused by exposure to irritants or in obesity also encourages protumoral activity.

Thus, during the attack of the organism causing inflammation, it is important to trigger the resolution of the inflammation; if the inflammation is not completely resolved, the inflammation may become chronic, leading to the aforementioned pathologies.

If the inflammatory mediators are essential to anti-tumoral surveillance, in particular during the cancerous immunoediting phase, allowing adapted anti-tumoral immunitary responses to be established, the latter can play a protumoral role, in particular the TNF (tumor necrosis factor). Indeed the tumoral inflammatory microenvironment may encourage tumor growth, angiogenesis, the invasion and formation of metastases. The tumor development is a result of the invasion of tumor cells due to an increased proliferation of cancerous cells, their resistance to death via apoptosis and angiogenesis in the tumoral microenvironment.

For example, the TNF may encourage the attraction of regulatory T cells (Tregs) in the tumor as well as myeloid-derived suppressor cells (MDSCs), weakening the anti-tumoral response further. Paradoxically, whilst cytotoxic therapies which induce the immunogenic death of tumor cells have made it possible to demonstrate the major role of the immune system in the choice of conventional anticancer treatments, the same approaches will now be described as associating the secondary pro-tumor effects through the dead cells killed by these therapies which would stimulate tumor growth.

In chronic inflammatory diseases, deregulating the resolution of the inflammation also remains a therapeutic avenue of choice for reactivating the natural resolution of the inflammation, i.e. permitting the arrest of the inflammatory response. At the present time, targeted therapeutic approaches of neutralizing or destroying the inflammatory factors have been shown to have limitations. Furthermore, it seems to be illusory to be able to control a complex pathology such as Crohn's disease solely by neutralizing an inflammatory factor, which is only a consequence of the pathology. However, resolving the inflammation by reestablishing an effective resolution could make it possible to treat the core of the inflammatory reaction.

Thus encouraging the resolution of inflammation and improving the elimination of tumor cells killed by anticancer treatments has become a major challenge in cancer care. In the same manner targeting the resolution of inflammation could make it possible to control the root cause of the inflammatory pathology.

The invention relates in particular to methods for preventing cancer by administering a resolutome, i.e. a combination of pro-resolution factors, capable of triggering the resolution of the inflammation, by inhibiting the escape of the tumor from immune surveillance and its development, and by reestablishing effective anti-tumor immunity.

Patent EP 2 941 257 describes a pharmaceutical preparation for use in the prevention or treatment of a pathological immune response; this pharmaceutical preparation comprises a supernatant which can be obtained from the coculture of phagocytes with apoptotic cells. In this patent, the pharmaceutical preparation is used in the treatment of a pathology such an autoimmune disease, for example rheumatoid arthritis (RA) or chronic inflammatory diseases of the intestine (chronic inflammatory bowel disease—CIBD). This pharmaceutical preparation is also used to treat graft-versus-host disease (GVHD).

The present invention has a different aim, namely a method for resolving protumoral inflammation by means of a supernatant obtained by a coculture of irradiated macrophages and leucocytes; this supernatant has in an unexpected manner numerous advantages over the supernatant described in patent EP 2 941 257. In particular, it provides a greater quantity of pro-resolution factors than is the case with the supernatant of the aforementioned patent (FIG. 1a); it also has biological superiority (FIG. 1b).

SUMMARY

The pharmaceutical preparation according to the invention can be used in cases where resolution has failed, in order to reestablish an effective resolution and permit an arrest of the inflammatory reaction. The aims of the invention are therefore in particular that of resolving chronic inflammation and resolving inflammation which encourages tumor growth by means of the aforementioned pharmaceutical preparation.

The present invention is based first of all on the fact that targeting the resolution of protumoral inflammation makes it possible to restore the anti-tumor immune response and stop the chronic anti-inflammatory reaction.

It should be remembered at this stage that inflammation is beneficial when a tumor starts to become established but after this has a negative effect encouraging treatment failure, which the present invention is aiming to control.

A method according to the present invention consists of using a supernatant obtained by generating macrophages derived from monocytes from leucocytes, and storing them with leucocytes which have been previously irradiated, thus enabling their coculture, and collecting factors contained in the supernatant produced by the cells.

The supernatant of the pharmaceutical preparation according to the invention which is intended to resolve the inflammation, will be referred to as "Resolvix" in the following description.

The injection of these factors makes it possible to resolve the active inflammatory reaction in a plurality of experimental models (arthritis, inflammatory bowel disease—IBD, colitis, experimental autoimmune encephalomyelitis), but also to encourage tissue repair. In an interesting manner, this approach also makes it possible to restore anti-cancer immunity and thus encourage tumoral regression.

By way of a non-limiting example, a method for producing the supernatant according to the invention (Resolvix) will now be described.

The leucocytes are isolated on D0 by density gradient from whole blood, washed, resuspended in a defined culture medium generally used by a person skilled in the art in the present technical field, which has a salt, amino acid and vitamin base, such as for example the medium known as RPMI 1640, then apportioned 60% into a first pocket and 40% into a second. The first pocket then receives a differentiating factor, which can be M-CSF (Macrophages Colony-Stimulating Factor), and is preserved in conditions which preserve cellular viability, for example at 37° C., 5% $CO_2$, for several days, preferably 3, then again receives the aforementioned defined fresh culture medium. Said first pocket is then left as it is, resulting in the production of macrophages after several days of preservation, preferably 4 days, in conditions that preserve cellular viability, for example at 37° C., 5% $CO_2$. The second pocket is in turn preserved at a low temperature, preferably at a temperature below +10° C., and more preferably below +5° C. On the 7th day, the second pocket is irradiated, for example by means of X-rays, then the first and the second pocket are released from their medium. The second pocket is then put in a secretion medium, which has a salt, amino acid and vitamin base, known by a person skilled in the art, such as for example one known as MEM, and transferred into the first for storage in conditions that preserve cellular viability, for example at 37° C., 5% $CO_2$. During this storage period the coculture takes place resulting in the production of a conditioned supernatant, which can take several days, preferably 2. In the present description, a "conditioned supernatant" is a supernatant containing factors derived from cells. Following this period of coculture, the supernatant is collected in a new pocket, filtered then preserved at a very low temperature, preferably in the region of −80° C. This supernatant is then advantageously mixed with other produced supernatants, according to the method described above, from buffy coats resulting from other blood donors, then this mixture is apportioned into unit doses, lyophilized or not lyophilized, then stored.

BRIEF DESCRIPTION OF THE DRAWINGS

In a more precise manner, in vivo models of tumor growth were used. The results obtained are shown in the following figures.

\*=p<0.05, \*\*=p<0.01 & \*\*\*=p<0.001 vs vehicle, 2way ANOVA test.

Figure 4:
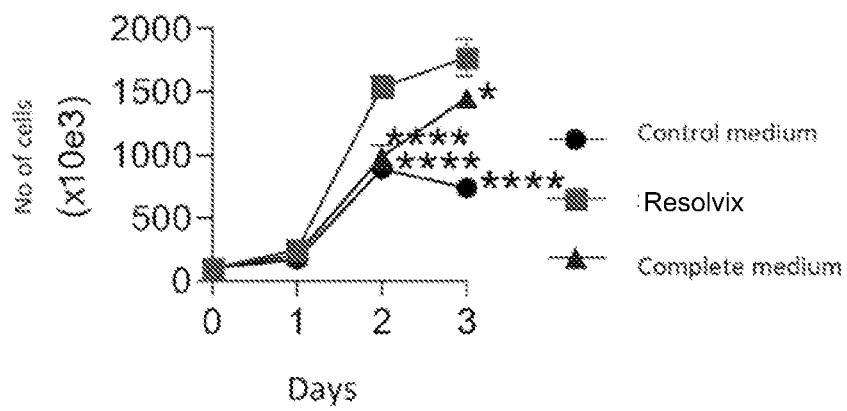

FIG. 4: evolution of in vitro cell proliferation of the cancerous cell line EL-4 in the presence of Resolvix. The cellular proliferation was evaluated by a cell count every day for 3 days. The data are from a representative experiment of two, expressed as an mean of triplicates+/−standard error of the mean.\*=p<0.05, \*\*\*\*=p<0.0001 vs Resolvix, 2way ANOVA test.

Figure 5:
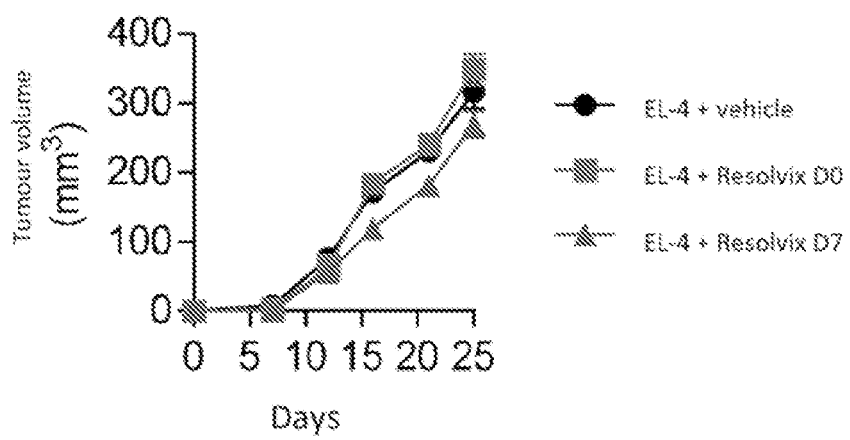

FIG. 5: Resolvix treatment of solid tumors in immunodeficient mice. The volume (in mm3) of tumors induced by the cancer line EL-4 subcutaneously into the right abdominal flank of immunodeficient mice RAG-γ/c, was determined at different times. Resolvix was injected either on the date of injection of cancer cells (D0) or 7 days later (D7). The data are from an experiment with 5 animals per group, expressed as the mean+/−standard error of the mean.

DETAILED DESCRIPTION OF THE PREFERRED EMBODIMENTS

Figure 1:
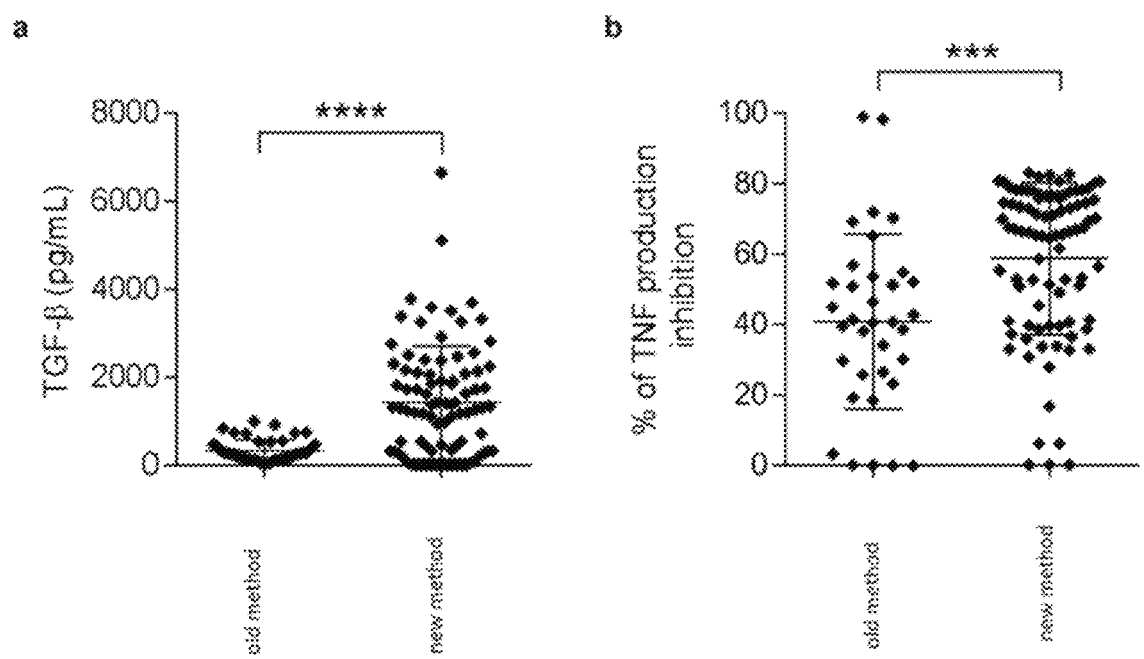
FIG. 1: biological and activity comparison of the new method of production resulting in the supernatant named Resolvix. The new method of production makes it possible to obtain a greater quantity of pro-resolution factors such as the anti-inflammatory cytokine TGF-beta, quantified by the ELISA test (a), and a biological superiority (b) evaluated by the biological test inhibiting the production of TNF in monocytes stimulated by phytohaemagglutinin. Data from 35 samples of the old method and 89 of the new method, expressed as a % of the inhibition of TNF production, represented by the mean+/−standard error of the mean. \*\*\*=p<0.001, \*\*\*\*=p<0.0001, unpaired Student's t-test. In this Figure, the old method relates to the method resulting in the supernatant described in the aforementioned patent EP 2 941 257.

Said data demonstrate in an interesting manner that the injection of Resolvix in mice carrying T lymphoma leukemia (tumor line EL4-luciferase+ enabling tracking of the tumor growth by bio-imaging) results in a regression of tumor growth (FIG. 1).

Figure 2:
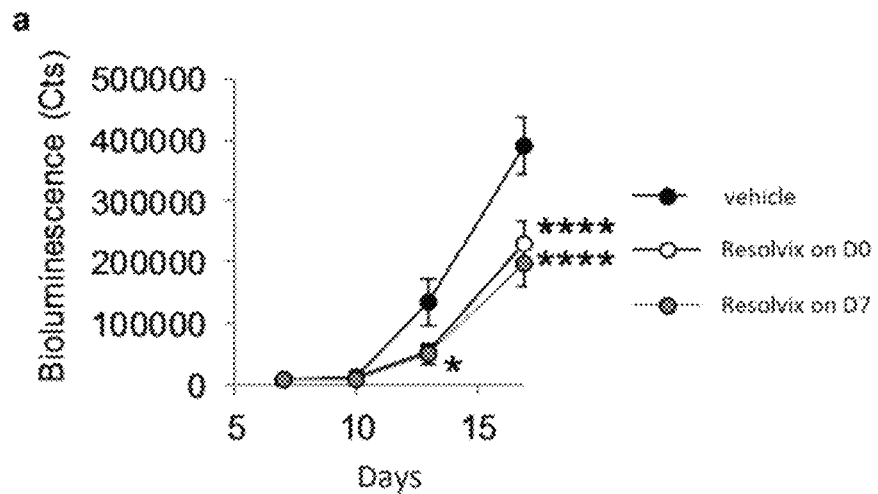
FIG. 2: tracking tumor growth. The bioluminescence emitted by the tumoral line EL4-Luc+ (after injection of luciferase) has been quantified in mice C57Bl/6 with leukemia, treated or not treated with Resolvix on D0 or D7 after injection of leukemia cells (a). Data resulting from a representative experience of two with 5 animals per group, expressed as a group mean+/−standard error of the mean. \*=p<0.05, \*\*\*\*=p<0.0001, vs vehicle, 2way ANOVA test. Representative images of bio luminescence of 5 untreated mice (vehicle) and 5 mice who have received Resolvix on D0, acquired 21 days after the injection of tumor cells, are shown (b). The intensity of the luminescence emitted (from dark grey to light grey) is associated proportionally with the number of tumor cells that have proliferated.
Figure 2:
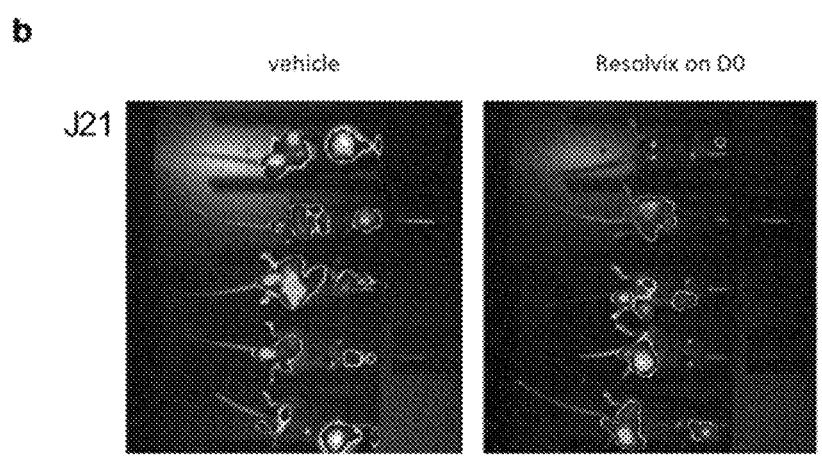

These same observations were made in a second model, with solid tumors (tumor lines EL-4 or B16-OVA injected subcutaneously), in which the injection of Resolvix makes it possible to reduce the size of tumors (FIG. 2).

Figure 3:
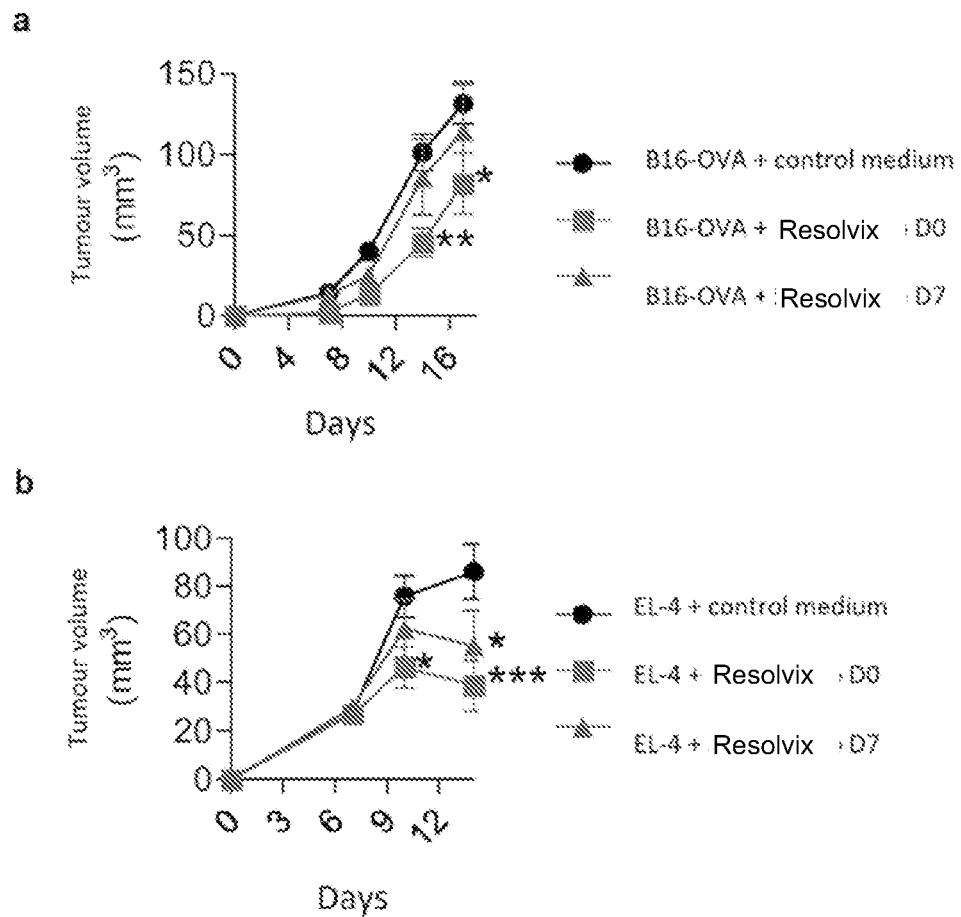
FIG. 3: evolution of tumors after treatment with Resolvix. The volume of the tumors (in mm3) was evaluated from the injection of tumor line B16-OVA (a) or from tumor line EL-4 (b) subcutaneously into the right abdominal flank of mice C57Bl/6 over time. Resolvix was injected either on the date of injection of cancer cells (J0), or 7 days later (J7). Data from 2 experiments (a and b) representative of 6 with 5 animals per group, expressed as a mean+/−standard error of the mean.

These results suggest that the Resolvix treatment could directly influence the growth of the tumor line in vivo, by means of a direct cytotoxic effect. In order to evaluate this possibility, additional experiments in vitro have been performed and have shown that the culture of tumor cells EL-4 in the presence of Resolvix encourages rather the growth of the line (FIG. 3). These data show that the inhibition of the tumor growth observed in vivo after treatment with Resolvix is not linked to a direct cytotoxic effect of the drug on the tumor cells.

Furthermore, the fact that the effect of the treatment is not directly on the tumor cells suggests that the restoration of anti-tumor immunity is due to the treatment. Indeed, in the absence of the immune system, i.e. in immunodeficient mice C57B1/6 RAG-γ/c with tumors, the Resolvix treatment has no effect on the in vivo tumor growth (FIG. 4).

The injection of Resolvix in the tumor models is performed at the time of grafting tumor cells (D0) or 7 days afterwards (D7). By thus controlling the inflammation at these different times, it is possible to control the tumor growth and reestablish anti-tumor immunity.

Thus, from the above it appears that the use of Resolvix according to the present invention makes it possible to restore anti-tumor immunity and/or stop tumor progression. More generally, the pharmaceutical preparation according to the invention can be used to target, control, inhibit, resolve inflammation associated with cancer, thus making it possible as just mentioned to restore anti-tumor immunity and/or to stop tumor progression.

The supernatant according to the invention can be used in particular in the treatment of cancers, either alone or along with other therapies, in human or veterinary medicine. The cancers are in particular those represented by lymphomas, leukemias, sarcomas and carcinomas, and more precisely T-cell lymphomas, B-cell lymphomas, melanomas and colon carcinomas.

The invention claimed is:

1. Pharmaceutical preparation of Resolvix used for controlling tumor progression or for restoring anti-tumor immunity, comprising:
    a supernatant obtained from a co-culture of leucocytes, the co-culture apportioned 60% and 40% respectively between
        a first portion comprising macrophages, and
        a second portion comprising irradiated leucocytes,
    wherein the leucocytes of the co-culture are isolated from the buffy coat resulting from whole blood,
    the first portion of the leucocytes is washed, resuspended in a defined culture medium of RPMI 1640, then placed in a first pocket receiving a Macrophages Colony-Stimulating Factor differentiation factor and preserved in conditions of 37° C. and 5% $CO_2$ which preserve cellular viability for 3 days, prior to again receiving fresh defined culture medium of RPMI 1640, then left as it is again in the conditions of 37° C. and 5% $CO_2$ which preserve cellular viability for 4 days, resulting in the production of macrophages,
    the second portion of the leucocytes is placed in a second pocket kept at a temperature below +5° C., and wherein the second portion is then irradiated in the second pocket on the seventh day,
    the second pocket, after having been freed from its irradiated medium, is then put in an MEM secretion medium comprising a salt, an amino acid, and a vitamin base, in conditions that preserve cellular viability,
    the second portion in the second pocket is transferred into the first portion in the first pocket, previously freed from its medium, to form the co-culture, the co-culture being stored for 2 days in conditions of 37° C. and 5% $CO_2$ that preserve cellular viability for forming the co-culture between the leucocytes for a period leading to the production of a conditioned supernatant,
    the resulting supernatant of the co-culture is collected in a new pocket, filtered and kept at approximately −80° C., and
    wherein based upon the pharmaceutical preparation, a concentration of TGF-beta and an inhibition of TNF production in monocytes stimulated by phytohaemagglutinin are increased, and the pharmaceutical preparation controls tumor progression in vivo.

2. A method of treating cancers using a pharmaceutical preparation of Resolvix for controlling tumor progression or for restoring anti-tumor immunity either alone or in addition to other anti-cancer therapies, comprising:
    administering the pharmaceutical preparation to a cancer patient,
    wherein the pharmaceutical preparation used for controlling tumor progression or for restoring anti-tumor immunity comprises a supernatant obtained from a co-culture of leucocytes, the co-culture apportioned 60% and 40% respectively between a first portion comprising macrophages and a second portion comprising irradiated leucocytes,
    the leucocytes of the co-culture are isolated from the buffy coat resulting from whole blood,
    the first portion of the leucocytes is washed, resuspended in a defined culture medium of RPMI 1640, then placed in a first pocket receiving a Macrophages Colony-Stimulating Factor differentiation factor and preserved in conditions of 37° C. and 5% $CO_2$ which preserve cellular viability for 3 days, prior to again receiving fresh defined culture medium of RPMI 1640, then left as it is again in the conditions of 37° C. and 5% $CO_2$ which preserve cellular viability for 4 days, resulting in the production of macrophages,
    the second portion of the leucocytes is placed in a second pocket kept at a temperature below +5° C., and wherein the second portion is then irradiated in the second pocket on the seventh day,
    the second pocket, after having been freed from its irradiated medium, is then put in an MEM secretion medium comprising a salt, an amino acid, and a vitamin base, in conditions that preserve cellular viability,
    the second portion in the second pocket is transferred into the first portion in the first pocket, previously freed from its medium, to form the co-culture, the co-culture being stored for 2 days in conditions of 37° C. and 5% $CO_2$ that preserve cellular viability for forming the co-culture between the leucocytes for a period leading to the production of a conditioned supernatant,
    the resulting supernatant of the co-culture is collected in a new pocket, filtered and kept at approximately −80° C., and
    wherein based upon the pharmaceutical preparation, a concentration of TGF-beta and an inhibition of TNF production in monocytes stimulated by phytohaemagglutinin are increased, and the pharmaceutical preparation controls tumor progression in vivo.

* * * * *